(12) United States Patent
Coyle et al.

(10) Patent No.: US 12,178,419 B2
(45) Date of Patent: Dec. 31, 2024

(54) COLLAPSIBLE MEDICAL DEVICE FOR ATRIAL SEALING AND TRANS-SEPTAL ACCESS

(71) Applicant: St. Jude Medical, Cardiology Division, Inc., St. Paul, MN (US)

(72) Inventors: Daniel Coyle, St Louis Park, MN (US); Daniel Goodman, Minnetonka, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 726 days.

(21) Appl. No.: 17/318,615

(22) Filed: May 12, 2021

(65) Prior Publication Data

US 2021/0259670 A1    Aug. 26, 2021

Related U.S. Application Data

(63) Continuation of application No. 16/059,726, filed on Aug. 9, 2018, now Pat. No. 11,006,938.
(Continued)

(51) Int. Cl.
*A61B 17/00* (2006.01)
*A61B 17/12* (2006.01)
*A61B 18/00* (2006.01)

(52) U.S. Cl.
CPC .... *A61B 17/0057* (2013.01); *A61B 17/12122* (2013.01); *A61B 2017/00243* (2013.01);
(Continued)

(58) Field of Classification Search
CPC .......... A61B 17/00234; A61B 17/0057; A61B 17/12122; A61B 2017/00243;
(Continued)

(56) References Cited

U.S. PATENT DOCUMENTS

2003/0220667 A1   11/2003   van der Burg et al.
2005/0288706 A1   12/2005   Widomski et al.
(Continued)

FOREIGN PATENT DOCUMENTS

EP    2316381 A2    5/2011
EP    2567663 A1    3/2013
(Continued)

OTHER PUBLICATIONS

"Atrial Fibrillation Market to Exhibit 13.26% CAGR to 2021 as Catheter Ablation Drives the AFib Industry Growth", Oct. 18, 2016, accessed at https://www.marketwatch.com/press-release/atrial-fibrillation-market-to-exhibit-1326-cagr-to-2021-as-catheter-ablation-drives-the-afib-industry-growth-2016-10-18-122034553.
(Continued)

*Primary Examiner* — Kankindi Rwego
(74) *Attorney, Agent, or Firm* — Armstrong Teasdale LLP

(57) ABSTRACT

The present disclosure provides collapsible medical devices that may be introduced via a delivery device into a pre-existing patent foramen ovale or trans-septal puncture hole and left in place to provide both a sealing function on the atrial wall and a septal-access function for additional procedures. The disclosed medical devices include a penetrable and re-sealable gasket material disposed in an open lumen in the medical device. This penetrable and re-sealable material allows catheters or other medical devices to pass therethough for providing additional therapy to an individual. By allowing the access point or portal to be opened by a guidewire or another medical tool, the medical devices as disclosed herein may be particularly suitable for a variety of cardiac procedures including, for example, atrial fibrillation, mitral valve replacement or repair, left atrial appendage closures, and the like.

20 Claims, 13 Drawing Sheets

Related U.S. Application Data

(60) Provisional application No. 62/543,663, filed on Aug. 10, 2017.

(52) U.S. Cl.
CPC ............ *A61B 2017/00247* (2013.01); *A61B 2017/00526* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00867* (2013.01); *A61B 2018/00351* (2013.01)

(58) Field of Classification Search
CPC .......... A61B 2017/00526; A61B 2017/00575; A61B 2017/00592; A61B 2017/00597; A61B 2017/00606; A61B 2017/00623; A61B 2017/00867; A61B 2018/00351
USPC ........................................................ 606/213
See application file for complete search history.

(56) References Cited

U.S. PATENT DOCUMENTS

| | | |
|---|---|---|
| 2007/0213813 A1 | 9/2007 | Von Segesser et al. |
| 2008/0200945 A1 | 8/2008 | Amplatz et al. |
| 2009/0281557 A1* | 11/2009 | Sander ............... A61B 17/3468 606/151 |
| 2012/0245623 A1 | 9/2012 | Kariniemi et al. |
| 2012/0253386 A1 | 10/2012 | Rowe et al. |
| 2012/0253389 A1 | 10/2012 | Rowe et al. |
| 2013/0331920 A1 | 12/2013 | Osypka |
| 2015/0272731 A1 | 10/2015 | Racchini et al. |
| 2016/0256141 A1 | 9/2016 | Mendez et al. |

FOREIGN PATENT DOCUMENTS

| | | |
|---|---|---|
| WO | 2016066180 A1 | 5/2016 |
| WO | 2016087504 A1 | 6/2016 |

OTHER PUBLICATIONS

"Atrial Septal Defect (ASD)", Cleveland Clinic, Mar. 12, 2015, accessed at https://my.clevelandclinic.org/health/diseases/11622-atrial-septal-defect-asd.

International Search Report and Written Opinion for International Patent Application No. PCT/US2018/045989, mailed Nov. 22, 2018, 17 pages.

Fisher et al. "The Incidence of Patent Foramen Ovale in 1,000 Consecutive Patients: A Contrast Transesophageal Echocardiography Study," Clinical Investigations 107(6), Jun. 1995, 1504-1509.

* cited by examiner

COLLAPSIBLE MEDICAL DEVICE FOR ATRIAL SEALING AND TRANS-SEPTAL ACCESS

CROSS-REFERENCE TO RELATED APPLICATIONS

This application is a continuation of U.S. patent application Ser. No. 16/059,726, filed Aug. 9, 2018, which claim priority to U.S. Provisional Patent Application No. 62/543,663, filed Aug. 10, 2017, which are incorporated by reference herein in their entirety.

BACKGROUND OF THE DISCLOSURE a. Field of Disclosure

The present disclosure generally relates to a collapsible medical device and methods of making and using the same. In particular, the present disclosure relates to a collapsible medical device that seals a patent foramen *ovale* or trans-septal hole and allows for repeated trans-septal access for subsequent medical procedures or therapies. The collapsible medical device includes a gasket that is penetrable and re-sealable disposed in a cylindrical segment of the device that provides both a sealing function and an access function. Methods of manufacturing and using the collapsible medical devices including the gasket are also disclosed.

b. Background Art

A wide variety of intravascular medical devices are used in various medical procedures within the body. Certain intravascular medical devices, such as catheters and guidewires, are generally used simply to deliver fluids or other medical devices to specific locations within a patient's body, such as a selective site within the vascular system. Other, frequently more complex, collapsible intravascular devices are used in treating specific conditions, such as devices used in removing vascular occlusions, for treating septal defects, for valve replacements, stent introduction, and the like. Many of these more complex collapsible intravascular devices are constructed, at least in part, of a braided tubular member, such as a nitinol braided tubular member.

SUMMARY OF THE DISCLOSURE

The present disclosure is directed to a collapsible medical device for occluding a trans-septal hole. The medical device comprises: (i) a tubular member formed of a braided fabric having a preset, expanded configuration and a collapsed configuration and comprising a proximal end and a distal end, wherein, in the expanded configuration, the tubular member comprises a proximal disc-shaped portion at the proximal end, a distal disc-shaped portion at the distal end, and a cylindrical segment between the proximal disc-shaped portion and the distal disc-shaped portion, wherein proximal free wire ends of the braided fabric extend proximally from the proximal disc-shaped portion and distal free wire ends of the braided fabric extend distally from the distal disc-shaped portion, the proximal and distal free wire ends and cylindrical segment collectively defining an open lumen through the tubular member, and (ii) a gasket disposed at least partially within the cylindrical segment, wherein the gasket occupies an entire length of the cylindrical segment and at least a portion of the open lumen defined by the proximal or distal free wire ends, the gasket sized and configured to be penetrable and re-sealable.

The present disclosure is also directed to a collapsible medical device for occluding a trans-septal hole. The medical device comprises: (i) a tubular member formed of a braided fabric having a preset, expanded configuration and a collapsed configuration and comprising a proximal end and a distal end, wherein, in the expanded configuration the tubular member comprises at least one plane of occlusion at the proximal end, at least one plane of occlusion at the distal end, and a segment therebetween, wherein proximal free wire ends of the braided fabric extend proximally from the at least one plane of occlusion at the proximal end and distal free wire ends of the braided fabric extend distally from the at least one plane of occlusion at the distal end, the proximal and distal free wire ends and the segment collectively defining an open lumen through the tubular member; and (ii) a gasket disposed at least partially within the segment, wherein the gasket occupies an entire length of the segment and at least a portion of the open lumen defined by the proximal or distal free wire ends, the gasket sized and configured to be penetrable and re-sealable.

The present disclosure is further directed to a method of forming a collapsible medical device for occluding a trans-septal hole. The method comprises: (i) introducing a braided fabric onto one or more mandrels; (ii) heat-setting the braided fabric on the one or more mandrels to form a structure with a proximal disc-shaped portion at the proximal end and a distal disc-shaped portion at the distal end of the structure and a cylindrical segment therebetween, wherein proximal free wire ends of the braided fabric extend proximally from the proximal disc-shaped portion and distal free wire ends extend distally from the distal disc-shaped portion, the proximal and distal free wire ends and the cylindrical segment collectively defining an open lumen through the structure; (iii) immobilizing the proximal and distal free wire ends of the structure; (iv) inserting a gasket into the cylindrical segment, wherein, once inserted, the gasket occupies an entire length of the cylindrical segment and at least a portion of the open lumen defined by the proximal or distal free wire ends; and (v) securing the gasket to the cylindrical segment.

The present disclosure is directed to a collapsible medical device for occluding a trans-septal hole. The medical device comprises: (i) a tubular member formed of a braided fabric having a preset, expanded configuration and a collapsed configuration and comprising a proximal end and a distal end, wherein, in the expanded configuration, the tubular member comprises a proximal disk-shaped portion at the proximal end, a distal disk-shaped portion at the distal end, and a cylindrical segment between the proximal disk-shaped portion and the distal disk-shaped portion; and (ii) a gasket disposed at least partially within the cylindrical segment, wherein the gasket is sized and configured to be penetrable and re-sealable.

The present disclosure is further directed to a collapsible medical device for occluding a trans-septal hole. The medical device comprises: (i) a tubular member formed of a braided fabric having a preset, expanded configuration and a collapsed configuration and comprising a proximal end and a distal end, wherein, in the expanded configuration the tubular member comprises at least one plane of occlusion at the proximal end, at least one plane of occlusion at the distal end, and a cylindrical segment therebetween; and (ii) a gasket disposed at least partially within the cylindrical segment, wherein the gasket is sized and configured to be penetrable and re-sealable.

The present disclosure is further directed to a method of forming a collapsible medical device for occluding a trans-septal hole. The method comprises: (i) inverting a proximal end of a braided tubular member over itself toward a distal end of the braided tubular member to form a structure having an inner layer and an outer layer, wherein the structure includes a free wire end; (ii) using one or more mandrels to form the structure to have a proximal disk-shaped portion at the proximal end and a distal disk-shaped portion at the distal end of the structure and a cylindrical segment therebetween; (iii) immobilizing the free wire end of the structure; (iv) introducing a gasket into the cylindrical segment; and (v) securing the gasket to the cylindrical segment.

The present disclosure is further directed to a method of forming a collapsible medical device for occluding a trans-septal hole. The method comprises: (i) introducing a braided tubular member onto one or more mandrels and forming a structure having a proximal disk-shaped portion at a proximal end and a distal disk-shaped portion at a distal end of the structure and a cylindrical segment therebetween, wherein the structure includes free wires ends at the proximal end and free wire ends at the distal end; (ii) immobilizing the free wire ends at the proximal end and distal end of the structure; (iii) introducing a gasket into the cylindrical segment; and (iv) securing the gasket to the cylindrical segment.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Figure 1:
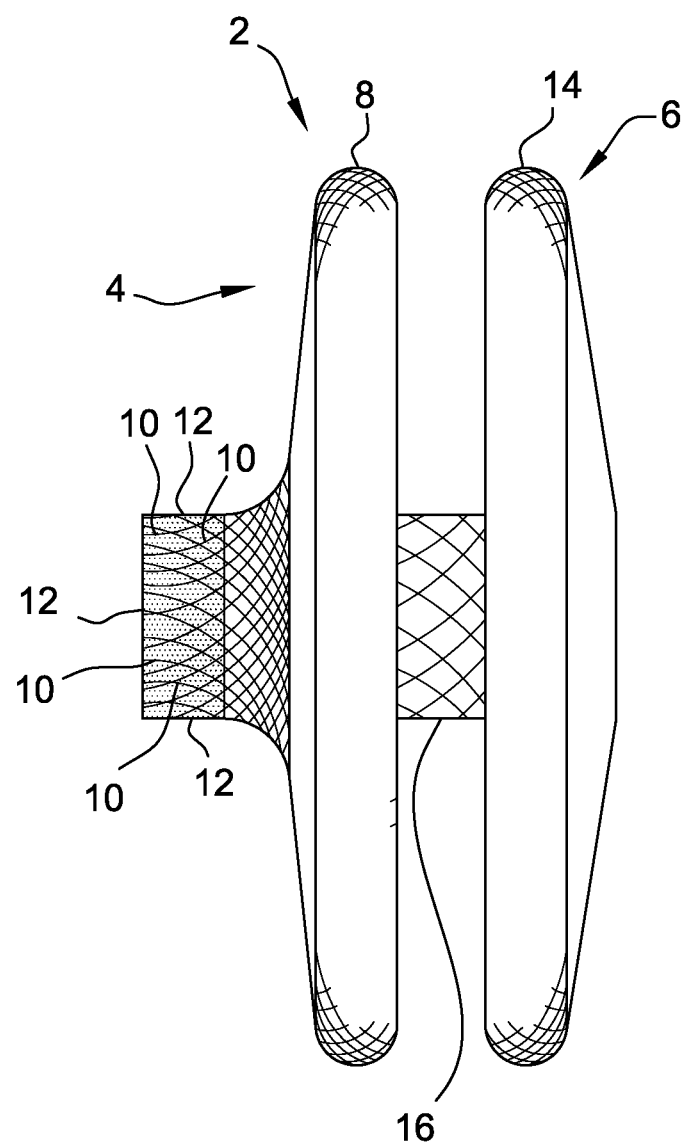
FIG. 1 is a perspective view of a structure of the present disclosure including a proximal disk, a distal disk, and a cylindrical segment.

Many cardiac procedures in use today are utilizing a trans-septal approach to deliver a particular medical device and/or one more types of cardiac therapies. If the individual being treated does not have a patent foramen *ovale* and a trans-septal puncture is needed for the desired access, the individual is left with a hole in the septum after the procedure, which could result in undesirable blood or blood clot crossover if not addressed properly. Further, if the individual requires an additional procedure or procedures in the future that require trans-septal access, an additional puncture may ultimately be required. As such, it would be beneficial to provide the individual with a medical device that could seal any trans-septal puncture hole or patent foramen *ovale*, yet allow for future trans-septal access for procedures so additional punctures would not be required or prevented by an occlusive device lacking an access point.

The present disclosure is directed to a collapsible medical device that may be introduced via a delivery catheter or other suitable medical delivery device into a pre-existing patent foramen *ovale*, trans-septal puncture hole, or the like and left in place to provide both a sealing function on the atrial wall and a septal-access function for additional procedures. That is, in addition to providing a desired sealing function to prevent blood clots from transferring across the atrial wall, the presently disclosed medical devices provide an access point or "portal" for crossing the trans-septal wall using a penetrable and re-sealable gasket material disposed in an open lumen in the collapsible medical device. This penetrable and re-sealable access point including the gasket material allows needles, catheters or other medical devices to pass therethough for providing additional therapy to an individual. By allowing the access point or portal to be opened by a guidewire or another medical tool, the medical devices as disclosed herein may be particularly suitable for a variety of cardiac procedures including, for example, atrial fibrillation, mitral valve replacement or repair, left atrial appendage closures, and the like.

The collapsible medical devices of the present disclosure including the penetrable and re-sealable gasket provide a user with a number of advantages. These devices create a pathway that can be utilized for multiple separate procedures at different times without the need to perform a trans-septal puncture each time, while providing a secure anchoring of the device in the desired position. Further, these devices can be manufactured in a wide variety of sizes (in a collapsible state) of from about 8 F to about 27 F to accommodate a range of end users and may include planes of occlusion as described herein (in an expanded state) of from about 4 millimeters to about 40 millimeters in size.

The collapsible medical devices of the present disclosure are formed from one or more layers of a tubular member formed of a braided fabric that comprises a plurality of wires generally configured to substantially occlude blood flow. The tubular member is generally formed of woven metal wires or strands that are heat set after formation into the desired configuration as more fully described below. The woven metal wires are a plurality of conventional wires that have a predetermined relative orientation between the wires. The wires define two sets of essentially parallel generally helical stands, with the strands of one set having a "hand", i.e., a direction of rotation, opposite that of the other set. These helical wires define a generally tubular metal fabric, known in the metal fabric industry as a tubular braid.

The pitch of the wires (i.e., the angle defined between the turns of the wire and the axis of the braid) and the pick of the fabric (i.e., the number of wire crossovers per unit length) may be adjusted as known by those of skill in the art based on the disclosure herein to increase/decrease/optimize the rigidity/strength as desired for a particular application.

The wires of the metal fabric used to construct the collapsible medical devices described herein are desirably formed of a material that is both resilient and that can be heat treated to substantially set a desired shape. Materials that are suitable for this purpose include a cobalt-based low thermal expansion alloy referred to in the field as Elgeloy, nickel-based high temperature high-strength superalloys commercially available from Haynes International under the trade name Hastelloy, nickel-based heat treatable alloys sold under the name Incoloy by International Nickel, and a number of different grades of stainless steel. An important factor in choosing a suitable material for the wires is that the wires retain a suitable amount of the deformation induced by a molding process when subjected to a predetermined heat treatment.

One class of materials that are desirable is memory-shape alloys. Such alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so.

One particularly desirable memory shape alloy for use in the present disclosure is nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." The elasticity of these alloys helps a medical device return to an expanded configuration for deployment inside of the body following passage in a distorted or collapsed form through a delivery catheter. Nitinol is a particularly desirable alloy for forming the collapsible medical devices of the present disclosure.

The metal wires used to fabricate the collapsible medical devices of the present disclosure may include wires having a diameter of from about 0.002 to about 0.008 inches (about 0.051 to about 0.203 millimeters), including from about 0.002 to about 0.005 inches (about 0.051 to about 0.127 millimeters). In some embodiments the wires have a diameter of from about 0.003 to about 0.0035 inches (about 0.076 to about 0.089 millimeters), and in some other embodiments, about 0.003 inches (about 0.076 millimeters). In one specific embodiment, the wires have a diameter of about 0.006 inches (about 0.152 millimeters). The number of wires in a wire mesh fabric (or tubular braid) may vary from about 36 to about 144, desirably from about 72 to about 144, and in some embodiments, 144. The pick count of the wire mesh may vary from about 30 to about 100, including from about 50 to about 80, including 70. As noted above, the wire diameter and the number of wires in the wire mesh fabric will tend to influence the rigidity, strength, and flexibility of the resulting collapsible medical device. Numerous other embodiments and combinations of wires sizes are contemplated within the scope of this disclosure.

In one specific embodiment of the present disclosure, a collapsible medical device including a penetrable and re-sealable gasket is formed from a tubular member formed of a braided fabric (such as a braided nitinol tube) by first inverting a proximal end of the braided fabric over itself toward a distal end thereof to form a structure having an inner layer and an outer layer. In this embodiment, the inversion creates a dual layer structure that includes only a single set of free wire ends; that is, one end of structure is smooth and contains no free wire ends due to the inversion.

Also disclosed and discussed hereinbelow is an alternative embodiment wherein a single layer or dual layer structure is created that includes free wire ends on both the proximal and the distal ends of the structure.

Once this dual layer structure including a single free wire end has been formed, it is introduced onto one or more mandrels and heat-set and/or heat-treated to shape and form the structure into the desired end form. In many embodiments of the present disclosure, the dual layer structure will be formed by the mandrel(s) to have a proximal disk-shaped portion at the proximal end and a distal disk-shaped portion at the distal end with a geometrical shaped segment or portion (sometimes referred to as a "waist") therebetween. This structure will include one set of free wire ends (open end of the braided structure), as discussed above, generally on the proximal end. In many embodiments, the geometrical shaped portion between the proximal disk-shaped portion and the distal disk-shaped portion may be a cylindrical segment or portion. The proximal disk-shaped portion and distal disk-shaped portion may be the same size, substantially the same size, or may be different sizes. Alternatively, in other embodiments, the proximal portion and the distal portion having the geometrical shaped segment therebetween may be geometrical shapes other than disks; the exact geometrical shape of the proximal portion and the distal portion is not critical, so long as they both provide a plane of occlusion and a secure fit. Although many of the embodiments disclosed and discussed herein refer to a proximal disk-shaped portion and a distal disk-shaped portion having a cylindrical segment therebetween, these portions and segment can be formed of any suitable geometrical shape that provides the intended benefit to the resulting medical device. In some embodiments, the proximal portion and the distal portion may be customized for an individual user based on a computerized tomography scan or other scan or procedure of the individual user.

Once the structure having the proximal disk-shaped portion at the proximal end and the distal disk-shaped portion at the distal end and the cylindrical segment therebetween has been formed using the mandrels and suitable heat treatment process, the free wires present on the proximal end of the structure are immobilized using a securement mechanism to ensure that the braided fabric does not unravel. The immobilization of the free wires may be done using any number of methods or securement mechanisms known in the art including, for example welding, soldering, brazing, heat shrink tubing, coating, gluing, tying, or affixing the ends together with a biocompatible cementitious organic material. In one desirable embodiment, the free wires may be immobilized by reflowing one or more materials over the free wires and allowing the reflowed material to harden. Suitable reflow materials include, for example, thermoplastic materials, with urethanes and polyether block amides (PEBAX®) being desirable materials. In many embodiments, the free wires will be immobilized and shaped such that an additional component may be introduced into the shaped hole or around the shaped hole to facilitate delivery of the medical device ultimately formed from the structure; that is, the free wires may be immobilized and shaped to allow a nut to be introduced into the formed hole so that a suitable delivery device could be attached to the nut for delivery of the medical device. In some embodiments, the nut, or another ring or other component or the free wires ends may be fabricated from a material (or coated with a material) that is radiopaque to facilitate guidance of the medical device during placement in a procedure. In some embodiments, the nut or other component may be introduced into the formed opening or hole prior to the reflowing of a material such that the reflowing of the material may immobilize the free wire ends and secure the nut or other component in place. In other embodiments, the free wire end may be trimmed or otherwise removed altogether so as to produce a flush end.

Referring now to FIG. 1, there is shown medical device 2 including proximal end 4 and distal end 6. Proximal end 4 includes proximal disk 8 and free wire ends 10 immobilized by coating 12. Distal end 6 includes distal disk 14. Located between proximal disk 8 and distal disk 14 is cylindrical segment 16. Although illustrated in FIG. 1 as two disks, proximal disk 8 and distal disk 14 could be any suitable geometric shape or shapes, as noted above.

Figure 1A:
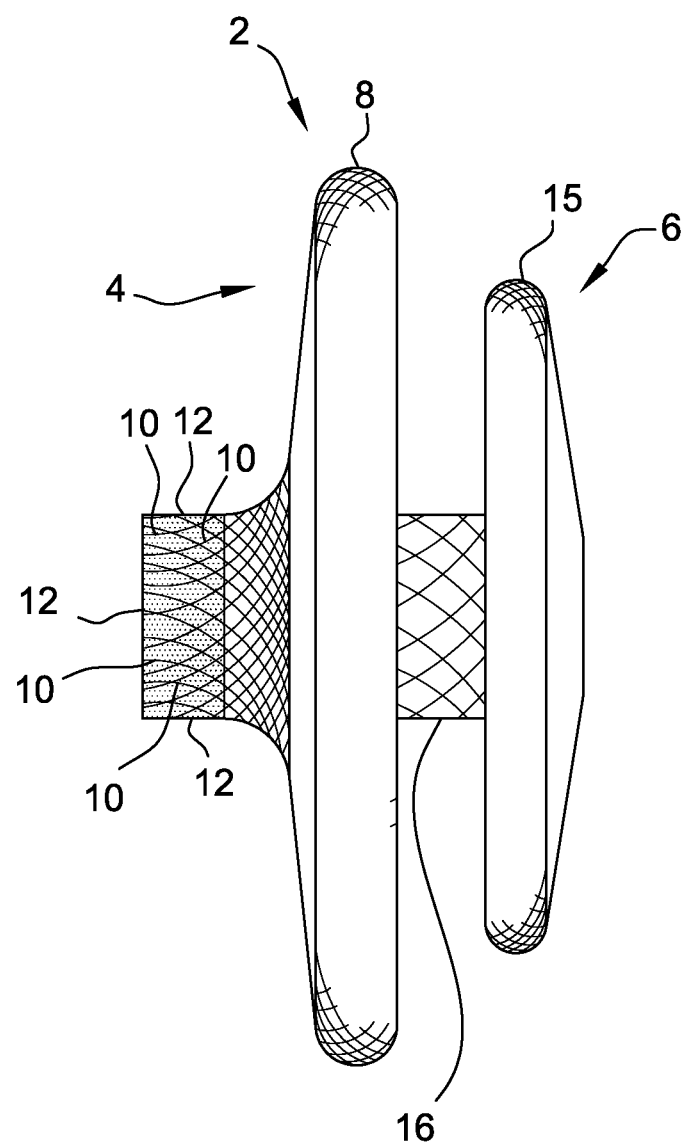
FIG. 1a is a perspective view of a structure of the present disclosure including a proximal disk, a distal disk, and a cylindrical segment, wherein the proximal disk and the distal disk are of different sizes.

Referring now to FIG. 1a, there is shown medical device 2 including proximal end 4 and distal end 6. Proximal end 4 includes proximal disk 8 and free wire ends 10 immobilized by coating 12. Distal end 6 includes distal disk 14. Located between proximal disk 8 and distal disk 14 is cylindrical segment 16. Proximal disk 8 and distal disk 14 are different sizes.

Figure 2:
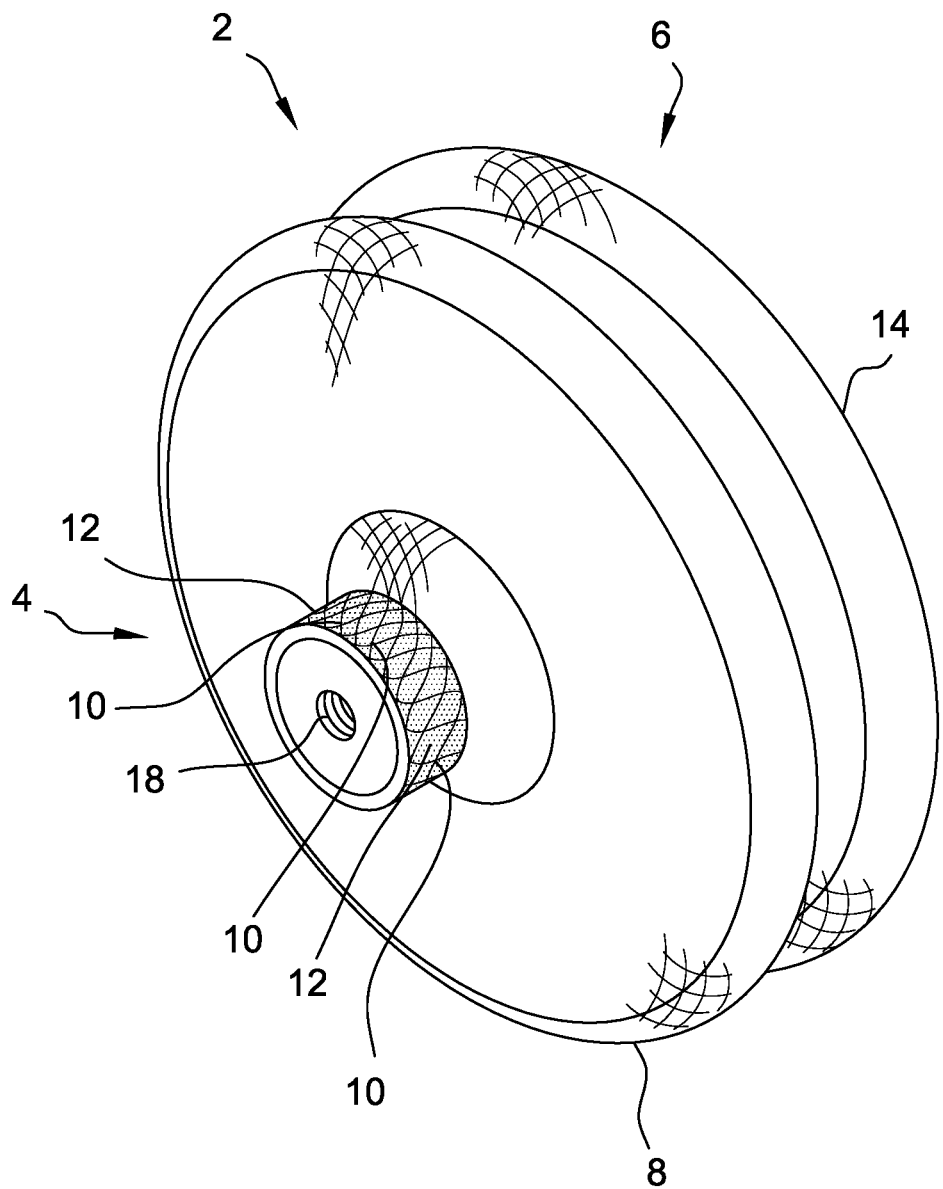
FIG. 2 is the structure of FIG. 1 shown from the proximal end.

Referring now to FIG. 2, there is shown a proximal end view of the structure of FIG. 1. Medical device 2 includes proximal end 4 and distal end 6. Proximal end 4 includes proximal disk 8 and free wire ends 10 immobilized by coating 12. Distal end 6 includes distal disk 14 having a continuous surface with no wire ends. Proximal end 4 additionally includes nut 18 located within free wire ends 10 for attaching another medical device (not shown) to medical device 2.

Once the free wires have been immobilized on the structure, a gasket is introduced into at least a portion of the cylindrical segment. The gasket is sized and configured to substantially occupy at least a portion of the cylindrical segment and provide a substantially tight fit within the structure that can provide the desired sealing function. The gasket may be introduced into the cylindrical segment such that the gasket occupies the entire length of the cylindrical segment, or only a part of the cylindrical segment; that is, the gasket may or may not completely fill the entire length of the cylindrical segment. Additionally, the gasket may or may not extend into and occupy part or all of the opening created by the immobilized wire ends; that is, the gasket may or may not extend into and occupy all or a portion of the cylindrical segment and part or all of the opening created by the immobilization of the wire ends.

The gasket is introduced into cylindrical segment of the structure to provide a sealing (and re-sealing after puncture) function as well as access through the structure; that is, the gasket seals the structure so that liquid cannot pass through while simultaneously providing a penetrable portal through which another medical device, such as a needle, catheter, or introducer may pass through without the sealing function of the disks or cylindrical segment being compromised. The other medical device, such as a needle, may also be withdrawn from the cylindrical segment at which time the gasket re-seals itself.

The gasket may be comprised of a single material, or it may be comprised of one or more materials such that it is a multi-part or multi-component gasket. It may be a single layer gasket, or it may be comprised of multiple layers. In some embodiments, the gasket may have a uniform density throughout, while in other embodiments the density of the gasket may change such that the gasket comprises zones of varying density. In some embodiments, all or one or more portions of the gasket may include one or more antithrombogenic coatings thereon to deter the formation of tissue or blot clots thereon. Additionally, the gasket may optionally include one or more pre-cut slits therein to facilitate penetration therethough by another medical device.

The gaskets for use in the present disclosure are generally formed from a self-sealing or self-healing material; that is, the gaskets are generally formed from one or more materials that are penetrable but that re-seal or re-close after the penetration is removed. Any number of suitable materials may be used to form the gasket including, for examples, polymers, silicone-based materials, soft thermoplastics, and the like. The exact material used to form the gasket is not critical, so long as it provides the desired penetrable and re-sealable characteristics described herein.

Once the gasket is positioned within the structure at the desired location within at least a portion of the cylindrical segment, the gasket may be stabilized and immobilized therein to ensure that the gasket remains in the desired location and is not substantially mobile within the structure. In one specific embodiment, the gasket is stabilized and immobilized within the structure by introducing one or more sutures through the tubular member of braided fabric and through the gasket such that the fabric and gasket are sutured together. Any number of sutures can be used for the stabilization and immobilization of the gasket. Other means of stabilizing and immobilizing the gasket may also be used in accordance with the present disclosure including for example, bonding, gluing, and the like.

Figure 3:
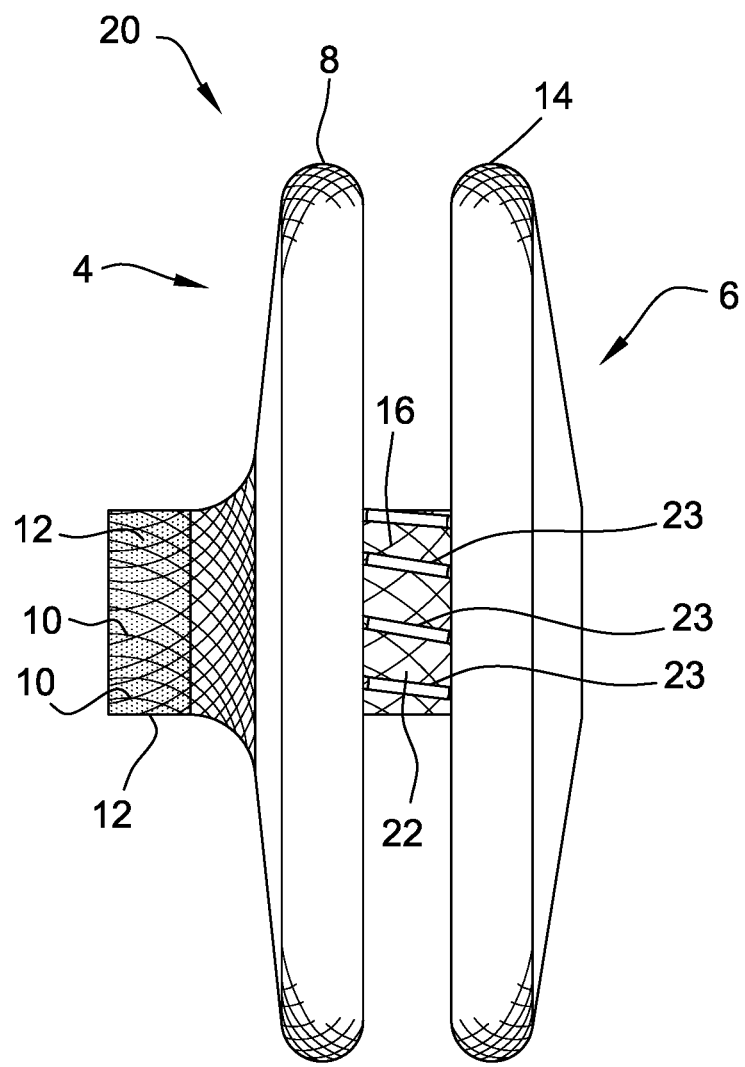
FIG. 3 is a perspective view of a collapsible medical device of the present disclosure including a penetrable and re-sealable gasket.

Referring now to FIG. 3, there is shown a collapsible medical device in accordance with one embodiment of the present disclosure. Collapsible medical device 20 includes proximal end 4 and distal end 6. Proximal end 4 includes proximal disk 8 and free wire ends 10 immobilized by coating 12. Distal end 6 includes distal disk 14. Located between proximal disk 8 and distal disk 14 is cylindrical segment 16. Disposed within cylindrical segment 16 is gasket 22. Gasket 22 is attached to cylindrical segment 16 with sutures 23.

Figure 4:
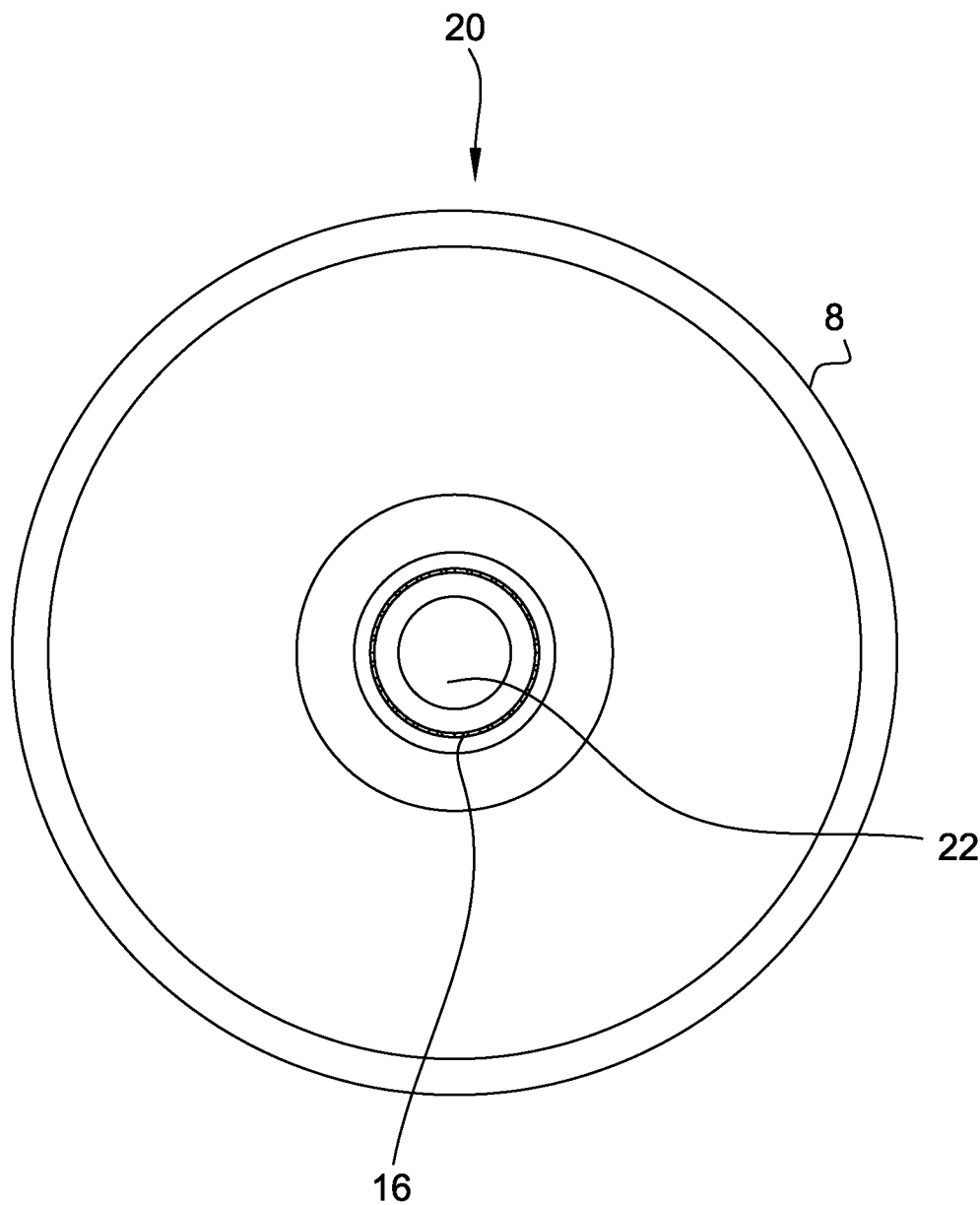
FIG. 4 is the collapsible medical device of FIG. 3 shown from the proximal end.

Referring now to FIG. 4, there is shown a proximal end view of collapsible medical device 20 of FIG. 3. Collapsible medical device 20 includes proximal disk 8 and gasket 22 disposed within the cylindrical segment 16.

In an alternative embodiment of the present disclosure, a collapsible medical device including a penetrable and re-sealable gasket as described above is formed from a single layer of a tubular member formed of a braided fabric (such as a braided nitinol tube) or a double layer of a tubular member formed of a braided fabric (one tubular member inside of another tubular member) without any inversion; that is, in this alternative embodiment, the tubular member or members formed of a braided fabric is not first inverted over itself as described above to create a dual layer structure. In this alternative embodiment, a single layer or a double layer structure is formed that includes two sets of free wire ends (two open ends of the braided fabric); one set on the proximal end, and one set on the distal end. This single layer or double layer of braided fabric including two sets of free wire ends is first introduced onto one or more mandrels and heat-set and/or heat-treated to shape and form the desired structure as set forth above. For example, in one embodiment, the single layer or double layer of braided fabric may be formed on the one or more mandrels to include a proximal disk-shaped portion at the proximal end, a distal disk-shaped portion at the distal end, and a cylindrical segment therebetween.

Once the structure having the proximal disk-shaped portion at the proximal end and the distal disk-shaped portion at the distal end and the cylindrical segment therebetween has been formed using the mandrels and suitable heat treatment process, the free wires present on the proximal end and the distal end are immobilized as described above to ensure that the fabric does not unravel at the proximal and distal ends. The same or different immobilization techniques may be used on each of the proximal and distal ends of the structure.

After the free wires have been immobilized on the proximal and distal ends of the structure, a gasket is introduced into at least a portion of the cylindrical segment as described above. The gasket is sized and configured to substantially occupy at least a portion of the cylindrical segment and provide a substantially tight fit within the structure that can provide the desired sealing function.

Figure 5:
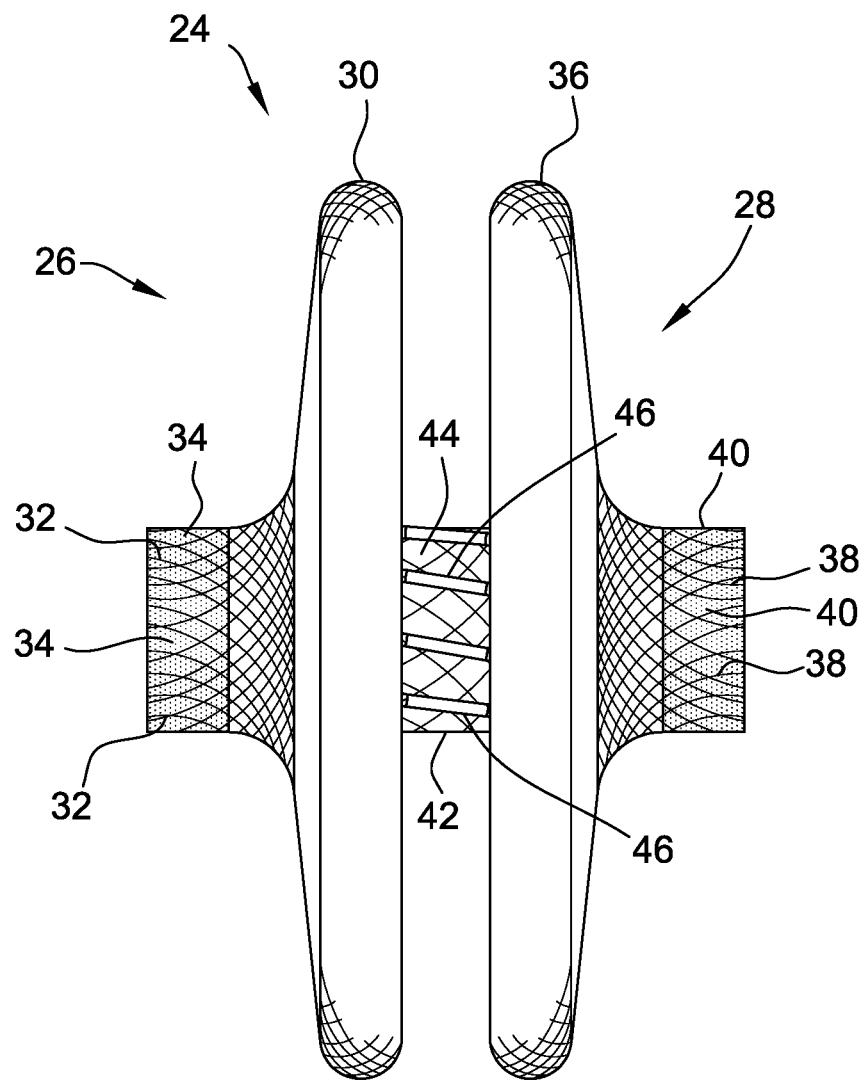
FIG. 5 is a perspective view of a collapsible medical device of the present disclosure including free wire ends on a proximal and a distal end.

Referring now to FIG. 5, there is shown a collapsible medical device 24 formed in accordance with this alternative embodiment wherein a single layer of braided fabric is utilized. Collapsible medical device 24 includes proximal end 26 and distal end 28. Proximal end 26 includes proximal disk 30 and free wire ends 32 immobilized by coating 34. Distal end 28 includes distal disk 36 and free wire ends 38 immobilized by coating 40. Located between proximal disk 30 and distal disk 36 is cylindrical segment 42. Disposed within cylindrical segment 42 is gasket 44. Gasket 44 is attached to cylindrical segment 42 with sutures 46.

Figure 6:
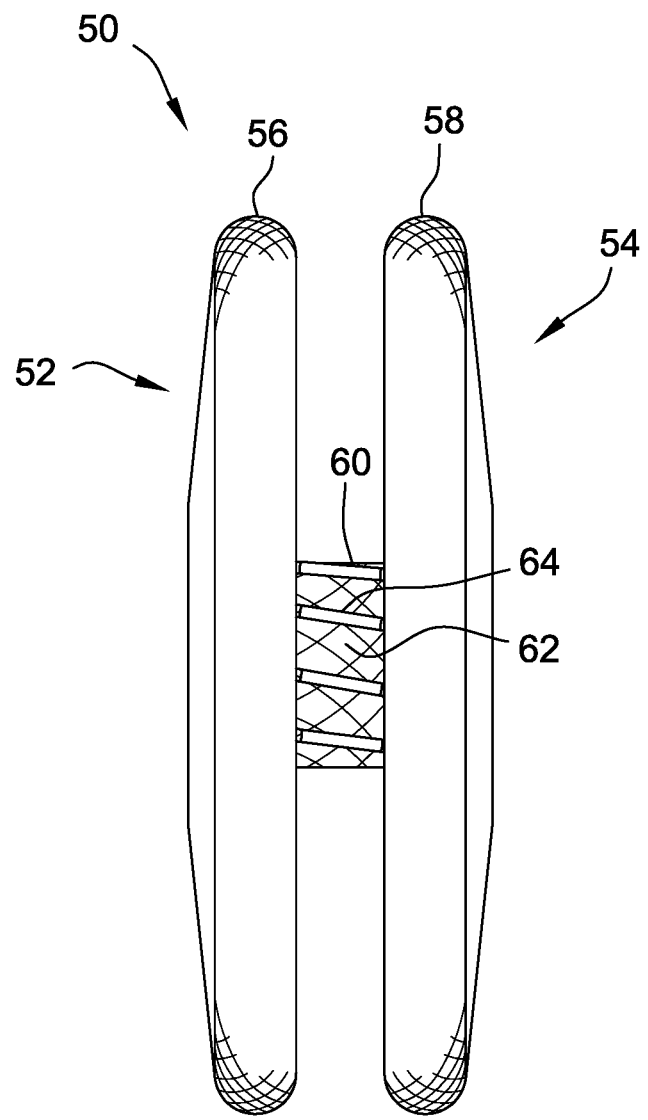
FIG. 6 is the collapsible medical device of FIG. 5 where the free wire ends on the proximal and distal end have been trimmed.

As noted above, in some embodiments of the present disclosure, the free wire end or ends on the collapsible medical device may be trimmed or otherwise removed altogether to reduce the overall profile of the resulting collapsible medical device, which may be advantageous in some embodiments where overall size is of concern. Such trimming may be accomplished by any means known to one of ordinary skill in the art so long as the remaining structure after the trimming is not subject to unraveling. Referring now to FIG. 6, there is shown one embodiment of a collapsible medical device of the present disclosure wherein the free wire ends on both the proximal end and the distal end have been trimmed away. Collapsible medical device 50 includes proximal end 52 and distal end 54. Proximal end 52 includes proximal disk 56. Distal end 54 includes distal disk 58. Located between proximal disk 56 and distal disk 58 is cylindrical segment 60. Disposed within cylindrical segment 60 is gasket 62. Gasket 62 is attached to cylindrical segment 60 with sutures 64.

Figure 7A:
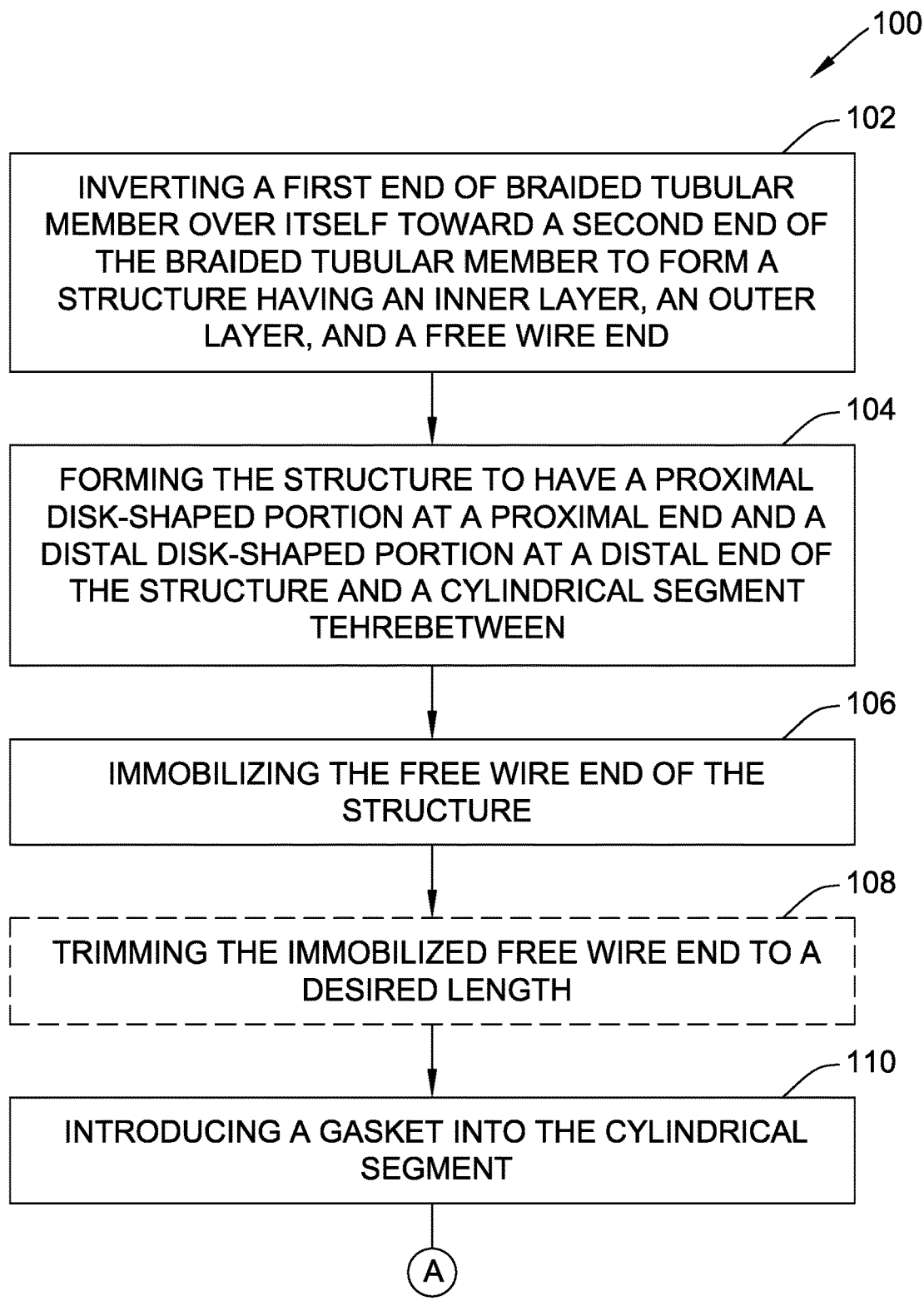
FIGS. 7A, 7B, 8A, and 8B are flow diagrams of methods of forming collapsible medical devices including a penetrable and re-sealable gasket.
Figure 7B:
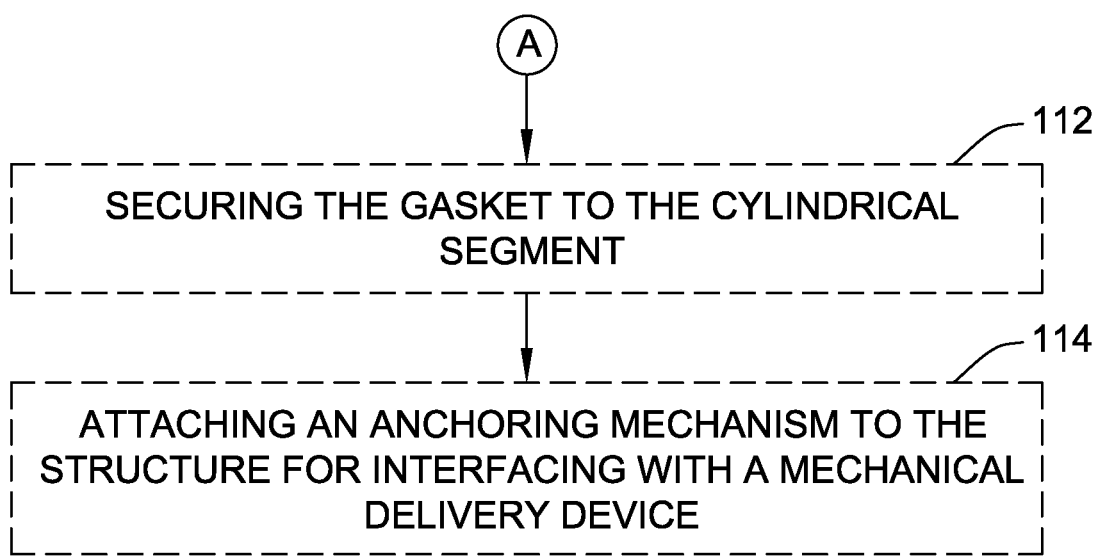

FIGS. 7A and 7B are flow diagrams of a method 100 for forming a collapsible medical device (such as collapsible medical device 20 shown in FIG. 3) including a penetrable and re-sealable gasket (such as gasket 22 shown in FIG. 3) for occluding a trans-septal hole, according to one embodiment. Method 100 includes inverting 102 a first (e.g. proximal) end of braided tubular member over itself toward a second (e.g. distal) end of the braided tubular member to form a structure having an inner layer, an outer layer, and a free wire end. Method 100 further includes forming 104 the structure to have a proximal disk-shaped portion at a proximal end and a distal disk-shaped portion at a distal end of the structure and a cylindrical segment therebetween (e.g. by using a mandrel). Method 100 further includes immobilizing 106 the free wire end of the structure. Method 100 further includes optionally trimming 108 the immobilized free wire end to a desired length. Method 100 further includes introducing 110 a gasket into the cylindrical segment and optionally securing 112 the gasket to the cylindrical segment. Finally, method 100 optionally includes attaching 114 an anchoring mechanism to the structure for interfacing with a medical delivery device.

Figure 8A:
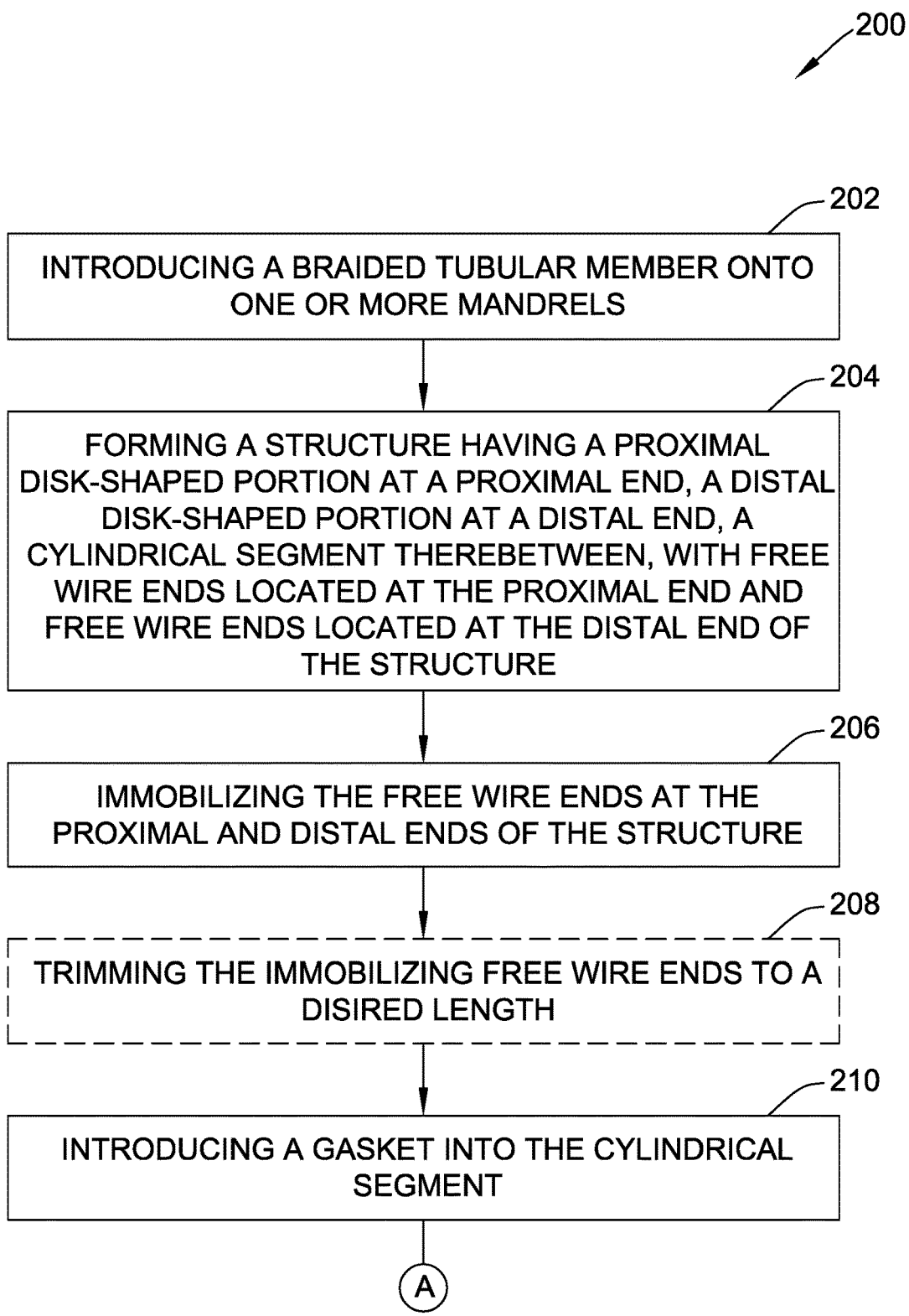
Figure 8B:
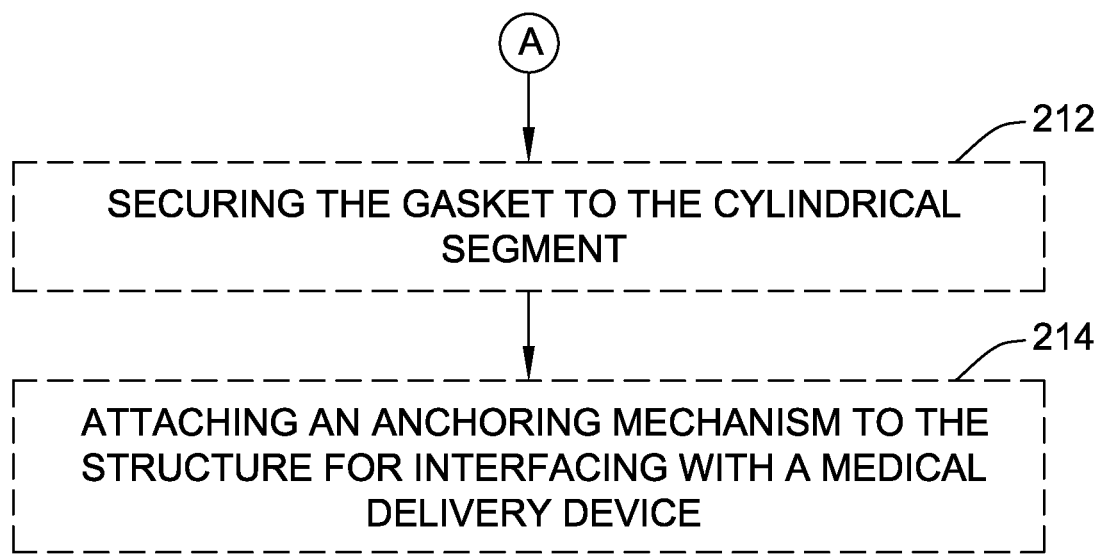

FIGS. 8A and 8B are flow diagrams of a method 200 for forming a collapsible medical device (such as collapsible medical device 24 shown in FIG. 5) including a penetrable and re-sealable gasket (such as gasket 44 shown in FIG. 5) for occluding a trans-septal hole, according to one embodiment. Method 200 includes introducing 202 a braided tubular member onto one or more mandrels and forming 204 a structure having a proximal disk-shaped portion at a proximal end, a distal disk-shaped portion at a distal end, a cylindrical segment therebetween, with free wire ends located at the proximal end and free wire ends located at the distal end of the structure. Method 200 further includes immobilizing 206 the free wire ends at the proximal and distal ends of the structure. Method 200 further includes optionally trimming 208 the immobilized free wire ends to a desired length. Method 200 further includes introducing 210 a gasket into the cylindrical segment and optionally securing 212 the gasket to the cylindrical segment. Finally, method 200 optionally includes attaching 214 an anchoring mechanism to the structure for interfacing with a medical delivery device.

As noted herein, the collapsible medical devices of the present disclosure including the penetrable and re-sealable gasket provide an access point or "portal" for crossing the trans-septal wall once introduced and deployed at a desired location within the body. In one exemplary embodiment of the present disclosure, the collapsible medical device is introduced into a pre-existing patent foramen *ovale* or trans-septal puncture hole and deployed as discussed herein such that the disks (or other planes of occlusion) present on the distal and proximal ends of the collapsible medical device, as well as the penetrable and re-sealable gasket, seal the patent foramen ovale or trans-septal puncture hole. Once the collapsible medical device including the penetrable and re-sealable gasket as described herein has been deployed, access across the septum (for further therapies and such as described herein) may be obtained by first locating and contacting the gasket with a guide catheter or similar delivery device and advancing a trans-septal puncture needle or equivalent through the guide catheter and through the length of the gasket. Once the trans-septal puncture needle has been advanced through the gasket, the guide catheter may be advanced over the trans-septal puncture needle and through the gasket. The needle may then be retracted resulting in the open guide catheter providing access across the collapsible medical device (and hence across the trans-septal wall) via the penetrable and re-sealable gasket. Additional medical devices and/or therapies may then be introduced through the guide catheter and across the trans-septal wall without the need for an additional trans-septal puncture hole. Once the additional medical devices and/or therapies have been used, they may be retracted out of the guide catheter and the guide catheter removed from the gasket. After the guide catheter is removed, the penetrable and re-sealable gasket will reseal itself and provide its desired sealing function while allowing for additional trans-septal access.

Figure 9A:
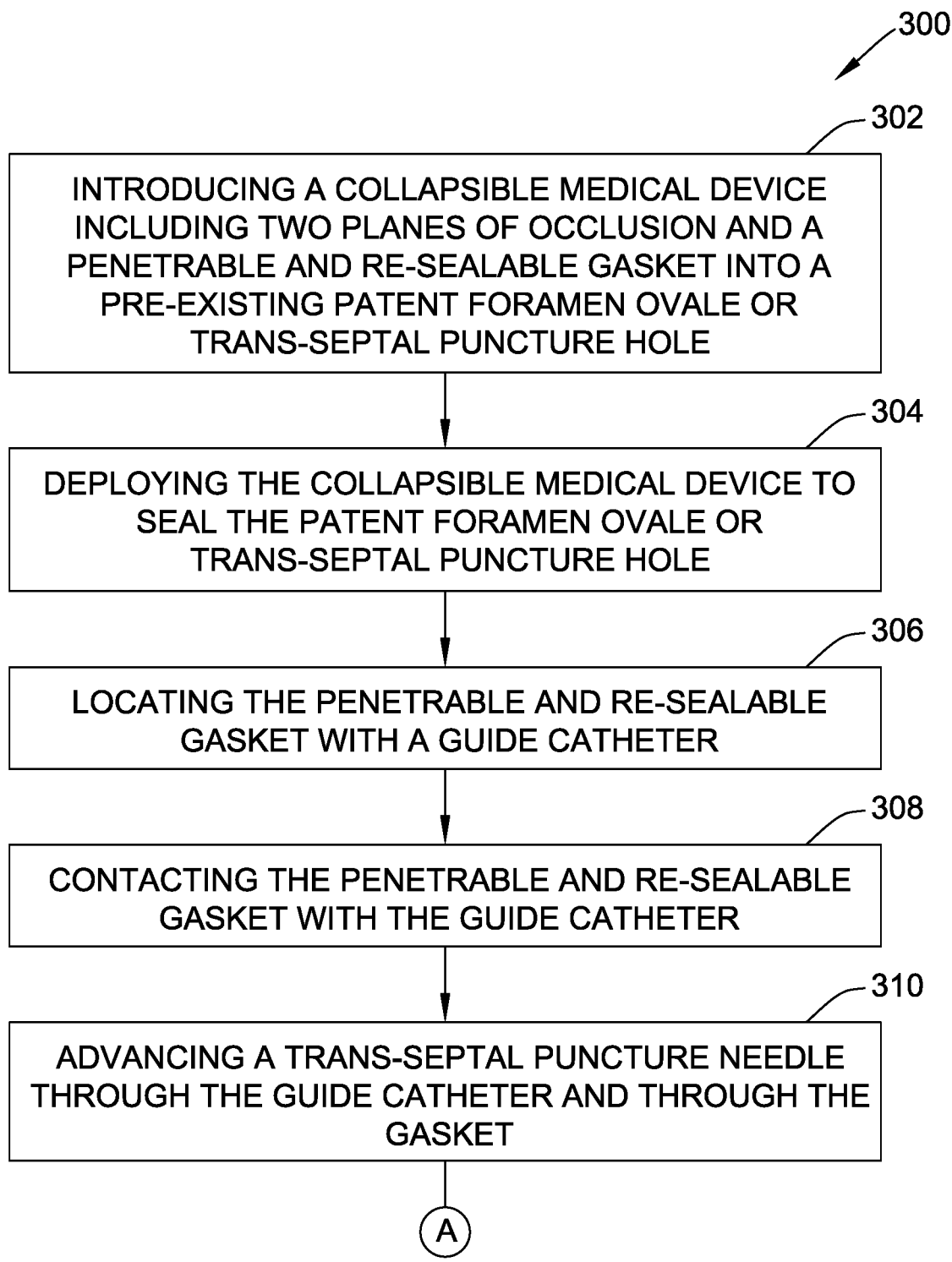
FIGS. 9A and 9B are flow diagrams of a method for crossing the trans-septal wall of an individual.
Figure 9B:
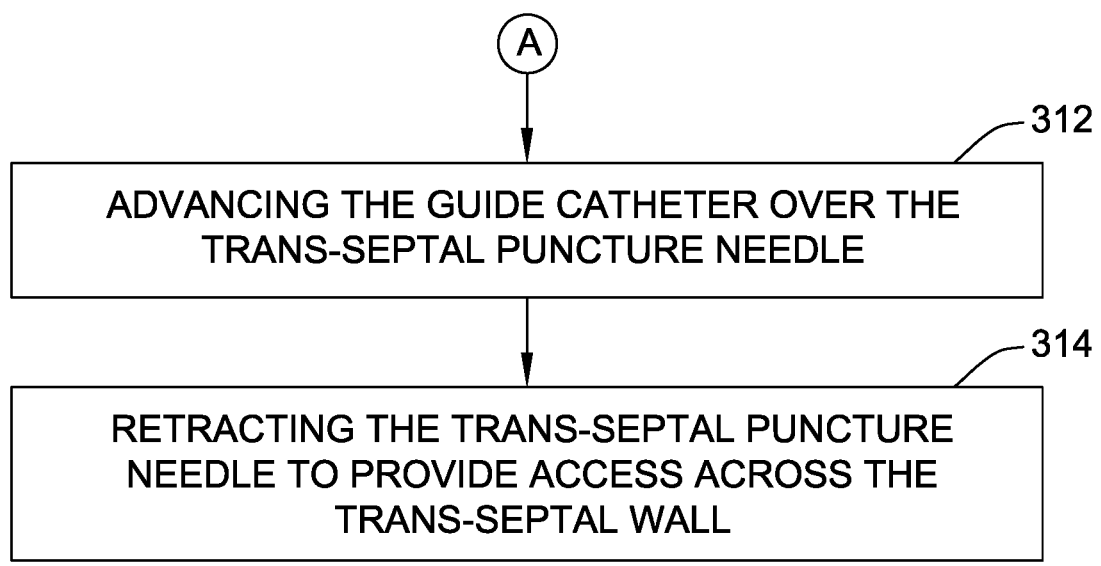

FIGS. 9A and 9B are flow diagrams of a method 300 for providing access across the trans-septal wall of an individual. Method 300 includes introducing 302 a collapsible medical device including two planes of occlusion and a penetrable and re-sealable gasket into a pre-existing patent foramen ovale or trans-septal puncture hole and deploying 304 the collapsible medical device to seal the patent foramen ovale or trans-septal puncture hole. Method 300 further includes locating 306 the penetrable and re-sealable gasket with a guide catheter and contacting 308 the penetrable and re-sealable gasket with the guide catheter. Method 300 further includes advancing 310 a trans-septal puncture needle through the guide catheter and through the gasket. Method 300 further includes advancing 312 the guide catheter over the trans-septal puncture needle and retracting 314 the trans-septal puncture needle to provide access across the trans-septal wall. In some embodiments, steps 306, 308, 310, 312, and 314 may be completed in a method separate and apart from steps 302 and 304; that is, they may be completed in a separate procedure by the same or a different operator.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A collapsible medical device for occluding a trans-septal hole comprising:
    a tubular member formed of a braided fabric having a preset, expanded configuration and a collapsed configuration and comprising a proximal end and a distal end, wherein, in the expanded configuration, the tubular member comprises a proximal disc-shaped portion adjacent to the proximal end, a distal disc-shaped portion adjacent to the distal end, and a cylindrical segment between the proximal disc-shaped portion and the distal disc-shaped portion, wherein proximal free wire ends of the braided fabric extend longitudinally proximally from the proximal disc-shaped portion to the proximal end of the tubular member and distal free wire ends of the braided fabric extend longitudinally distally from the distal disc-shaped portion to the distal end of the tubular member, the proximal and distal free wire ends and cylindrical segment collectively defining an open lumen through the tubular member; and
    a gasket disposed at least partially within the cylindrical segment, wherein the gasket extends into and occupies at least a portion of the open lumen defined by the proximal or distal free wire ends, the gasket sized and configured to be penetrable and re-scalable.

2. The collapsible medical device of claim 1, wherein the tubular member is formed from a single layer of braided fabric.

3. The collapsible medical device of claim 1, wherein the open lumen is concentric with the proximal and distal disc-shaped portions.

4. The collapsible medical device of claim 1, further comprising:
    a securement mechanism on at least one of the proximal or the distal end of the tubular member for immobilizing the respective at least one of the proximal or distal free wire ends.

5. The collapsible medical device of claim 4, wherein the securement mechanism comprises a coating.

6. The collapsible medical device of claim 1, wherein the gasket is secured to the cylindrical segment using one or more sutures.

7. The collapsible medical device of claim 1, wherein the gasket is comprised of a substantially self-sealing material.

8. The collapsible medical device of claim 1, wherein the gasket includes one or more pre-cut slits therein to facilitate penetration therethrough by another medical device.

9. The collapsible medical device of claim 1, wherein the gasket includes an antithrombogenic coating thereon.

10. The collapsible medical device of claim 1, wherein the gasket has a uniform density.

11. The collapsible medical device of claim 1, wherein the gasket has a non-uniform density.

12. The collapsible medical device of claim 1, wherein the proximal disc-shaped portion and the distal disc-shaped portion are substantially the same size, or wherein the proximal disc-shaped portion and the distal disc-shaped portion are different sizes.

13. The collapsible medical device of claim 1, wherein the cylindrical segment extends from the proximal disc-shaped portion to the distal disc-shaped portion, and wherein the gasket occupies an entire length of the cylindrical segment.

14. The collapsible medical device of claim 1, further comprising an additional component coupled to the proximal free wire ends within the open lumen, wherein the additional component is sized and configured to interface with a delivery device to deliver the collapsible medical device to the trans-septal hole.

15. A collapsible medical device for occluding a trans-septal hole comprising:
    a tubular member formed of a braided fabric having a preset, expanded configuration and a collapsed configuration and comprising a proximal end and a distal end, wherein, in the expanded configuration the tubular member comprises at least one first plane of occlusion adjacent to the proximal end, at least one second plane of occlusion adjacent to the distal end, and a segment therebetween, wherein proximal free wire ends of the braided fabric extend longitudinally proximally from the at least one first plane of occlusion to the proximal end of the tubular member and distal free wire ends of the braided fabric extend longitudinally distally from the at least one second plane of occlusion to the distal end of the tubular member, the proximal and distal free wire ends and the segment collectively defining an open lumen through the tubular member; and a gasket disposed at least partially within the segment, wherein the gasket extends into and occupies at least a portion of the open lumen defined by the proximal or distal free wire ends, the gasket sized and configured to be penetrable and re-sealable.

16. The collapsible medical device of claim 15, wherein the gasket is secured to the segment using one or more sutures.

17. The collapsible medical device of claim 15, wherein the gasket is comprised of a substantially self-sealing material.

18. The collapsible medical device of claim 15, wherein the gasket includes an antithrombogenic coating thereon.

19. A method of forming a collapsible medical device for occluding a trans-septal hole, the method comprising:
   introducing a braided fabric onto one or more mandrels;
   heat-setting the braided fabric on the one or more mandrels to form a tubular structure with a proximal disc-shaped portion adjacent to a proximal end of the structure and a distal disc-shaped portion adjacent to a distal end of the structure and a cylindrical segment therebetween, wherein proximal free wire ends of the braided fabric extend longitudinally proximally from the proximal disc-shaped portion to the proximal end of the tubular structure and distal free wire ends extend longitudinally distally from the distal disc-shaped portion to the distal end of the tubular structure, the proximal and distal free wire ends and the cylindrical segment collectively defining an open lumen through the tubular structure;
   immobilizing the proximal and distal free wire ends of the tubular structure;
   inserting a gasket through the open lumen into the tubular structure, wherein, once inserted, the gasket extends into and occupies at least a portion of the open lumen defined by the proximal or distal free wire ends; and
   securing the gasket to the tubular structure.

20. The method of claim 19, further comprising:
   attaching an additional component sized and configured to interface with a delivery device to the proximal free wire ends within the open lumen.

* * * * *

UNITED STATES PATENT AND TRADEMARK OFFICE
CERTIFICATE OF CORRECTION

| | |
|---|---|
| PATENT NO. | : 12,178,419 B2 |
| APPLICATION NO. | : 17/318615 |
| DATED | : December 31, 2024 |
| INVENTOR(S) | : Daniel Coyle et al. |

Page 1 of 1

It is certified that error appears in the above-identified patent and that said Letters Patent is hereby corrected as shown below:

In the Claims

In Claim 1, Column 12, Line 5, delete "re-scalable" and insert therefor -- re-sealable --

Signed and Sealed this
Twenty-fourth Day of June, 2025

Coke Morgan Stewart
*Acting Director of the United States Patent and Trademark Office*